United States Patent [19]

Siol et al.

[11] Patent Number: 5,976,527
[45] Date of Patent: Nov. 2, 1999

[54] HIGH SURFACE AREA SUPPORT HAVING BOUND LATEX PARTICLES CONTAINING OXIRANE GROUPS FOR IMMOBILIZATION OF SUBSTANCES

[75] Inventors: Werner Siol, Darmstadt-Eberstadt; Dieter Kraemer, Mainz; Norbert Suetterlin, Ober-Ramstadt; Cornelia Scordialo, Erzhausen; Gerhard Markert, Ober-Ramstadt; Erwin Schuster, Bensheim, all of Germany

[73] Assignee: Siol, Werner Roehm GmbH Chemishe Fabrik, Darmstadt, Germany

[21] Appl. No.: 07/990,554

[22] Filed: Dec. 14, 1992

Related U.S. Application Data

[63] Continuation of application No. 07/898,230, Jun. 12, 1992, abandoned, which is a continuation of application No. 07/744,666, Aug. 9, 1991, abandoned, which is a continuation of application No. 07/477,116, Feb. 7, 1990, abandoned, which is a continuation of application No. 07/364,483, Jun. 8, 1989, abandoned, which is a continuation of application No. 07/244,625, Sep. 12, 1988, abandoned, which is a continuation of application No. 07/119,297, Nov. 6, 1987, abandoned, which is a continuation of application No. 07/004,209, Jan. 5, 1987, abandoned, which is a continuation of application No. 06/837,336, Feb. 28, 1986, abandoned, which is a continuation of application No. 06/402,635, Jul. 28, 1982, abandoned.

[30] Foreign Application Priority Data

Aug. 5, 1991 [DE] Germany .................. 31 30 924

[51] Int. Cl.$^6$ .......................... A61K 38/43; C12N 11/14; C07K 17/14; G01N 33/551
[52] U.S. Cl. .................... 424/94.1; 424/94.6; 424/94.63; 424/94.61; 435/41; 435/176; 435/177; 435/180; 435/262.5; 436/524; 436/531; 514/2; 530/333; 530/402; 530/413; 530/811; 530/815
[58] Field of Search ................ 435/7, 176, 177, 435/180, 182, 262.5, 41; 436/524, 531, 532, 533, 534; 424/94.1, 94.6, 94.61, 94.63; 514/2; 530/333, 402, 413, 811, 815

[56] References Cited

U.S. PATENT DOCUMENTS

| | | | |
|---|---|---|---|
| 2,759,564 | 6/1956 | Conn et al. | 260/29.6 |
| 3,705,084 | 12/1972 | Reynolds | 195/63 |
| 4,067,959 | 1/1978 | Bolz | 435/7 |
| 4,102,746 | 7/1978 | Goldberg | 195/63 |
| 4,118,349 | 10/1978 | Bonacker et al. | 435/181 X |
| 4,168,250 | 9/1979 | Sutthoff et al. | 260/17.4 CL |
| 4,181,636 | 1/1980 | Fischer | 435/181 X |
| 4,193,910 | 3/1980 | Rohrbach et al. | 260/42.43 |
| 4,210,723 | 7/1980 | Dorman et al. | 435/180 |
| 4,218,363 | 8/1980 | Rohrbach et al. | 435/180 X |
| 4,226,747 | 10/1980 | Roncari | 435/180 X |
| 4,352,884 | 10/1982 | Nakashima et al. | 435/180 |
| 4,363,634 | 12/1982 | Schall, Jr. | 435/180 X |

FOREIGN PATENT DOCUMENTS

| | | |
|---|---|---|
| 1804159 | 7/1970 | Germany . |
| 1910488 | 9/1970 | Germany . |
| 1910532 | 9/1970 | Germany . |
| 2112740 | 10/1971 | Germany . |
| 2260184 | 7/1974 | Germany . |
| 8988/73 | 7/1973 | Japan . |
| 143281 | 11/1977 | Japan . |
| 77143281 | 11/1977 | Japan . |
| 12992/78 | 5/1978 | Japan . |
| 9008/71 | 6/1971 | Switzerland . |
| 545648 | 2/1977 | U.S.S.R. . |
| 1276006 | 6/1927 | United Kingdom . |
| 1274869 | 5/1972 | United Kingdom . |
| 1407720 | 9/1975 | United Kingdom . |

OTHER PUBLICATIONS

J. Kalal et al., Reactions of Epoxide Groups of Glycidyl Methacrylate Copolymers, J. Polymer Sci., Symposium No. 47, 155–166 (1974).
"Aeryl und tethacrylverbindungen", Rauch–Puntigam et al., Springer–Verlag, New York, 1967, pp. 228–229.
Kirk–Othmer, Encyclopedia of Chemical Technology, 3$^{rd}$ Ed., vol. 14, J. Wiley & Sons, New York, p. 90.
Biochemistry, Metzler, Iowa State University, p. 13.
Encyclopedia of Chemical Technology, Interscience Encyclopedia, Inc., New York, p. 865.
Gibbs, IndentificationMethods for Microbiologists, Academic Press, N.Y.1968 pp. 187–193.
DIN 53787.
Kirk–Othmer, op. cit., vol. 14, p. 90.
"Enzyme Engineering", Biotechnology and Bioengineering Symposium, No. 3, Interscience, p. 362.
Schildknecht, "Polymer Processes", Interscience, pp. 636–638.
Rauch–Puntigam, op. cit., p. 90.
Kirk–Othmer, op. cit., vol. 4, pp. 1–5.
Random House Dictionary, Unabridge Edn., Random House, New York, p. 149.
Chem. Abstr. 88, 132661t (1977).

*Primary Examiner*—David M. Naff

[57] ABSTRACT

A high surface area system is provided with latex particles for immobilization of substances containing nucleophilic groups. The high surface area system is formed by aggregating the latex particles or by bonding the latex particles to a porous support of high surface area. The latex particles contain groups such as oxirane groups that react with the nucleophilic groups. The substances containing nucleophilic groups may be enzymes or proteins such as albumin, immunoglobulins, blood-clotting factors, cell-membrane proteins or peptide hormones. The high surface area system may be used as a sorbent in removing pollutants, as a stationary phase in organic synthesis such as peptide synthesis, and in the therapeutic treatment of a patient.

32 Claims, No Drawings

5,976,527

HIGH SURFACE AREA SUPPORT HAVING BOUND LATEX PARTICLES CONTAINING OXIRANE GROUPS FOR IMMOBILIZATION OF SUBSTANCES

This is a continuation of Ser. No. 07/898,230, Jun. 12, 1992, abandoned, which is a continuation of Ser. No. 07/744,666, Aug. 9, 1991, abandoned, which is a continuation of Ser. No. 07/477,116, Feb. 7, 1990, abandoned, which is a continuation of Ser. No. 07/364,483, Jun. 8, 1989, abandoned, which is a continuation of Ser. No. 07/244,625, Sep. 12, 1988, abandoned, which is a continuation of Ser. No. 07/119,297, Nov. 6, 1987, abandoned, which is a continuation of Ser. No. 07/004,209, Jan. 5, 1987, abandoned, which is a continuation of Ser. No. 06/837,336, Feb. 28, 1986, abandoned, which is a continuation of Ser. No. 06/402,635, Jul. 28, 1982, abandoned.

BACKGROUND OF THE INVENTION

1. Field of the Invention

The invention relates to high-surface-area systems adaptable to the immobilization thereon of substrates containing nucleophilic groups, and more particularly to systems adaptable to the immobilization of biologically relevant substances and functional units.

2. Description of the Art

A "biologically relevant" material is one capable of interacting primarily with biological systems and is itself preferably of biological origin.

Both in pure research and in biotechnology, the immobilization of biomacromolecules on support or carrier molecules is among the subjects which have been receiving the closest attention.

So far as the immobilization of enzymes in particular is concerned, the immobilization techniques which have been proposed or are being employed may be classed as follows:

(1) Covalent bonding to a solid support or carrier phase;
(2) Covalent bonding to soluble polymers;
(3) Physical adsorption to a solid support or carrier phase;
(4) Crosslinking at solid surfaces;
(5) Crosslinking with difunctional reagents;
(6) Inclusion in a gel phase; and
(7) Encapsulation.

[See R. D. Falb in "Enzyme Engineering", Vol. II, Ed. E. K. Pye and L. B. Wingard, Plenum Press, 1974; U.S. Pat. No. 3,650,900; Melrose, Rev. Pure and Appl. Chem. 21, 83–119 (1971).]

The technique named under (1) above, covalent bonding to a solid support phase, has so far received the widest attention.

However, it is apparent from the pertinent literature that the manifold tasks which it was hoped could be performed through immobilization of biomacromolecules, such as the purification, separation, and binding of enzymes, the immobilization of microorganisms, affinity chromatography, immune reactions, tasks in clinical diagnostics, etc., cannot be carried out by a single technique. Even where solutions tailored to specific problems are available, as, for example, in the immobilization of specific enzymes on specific supports, translation from the laboratory scale to the technical scale often poses obstacles which are difficult to overcome.

For this reason, many attempts have been made to find solutions which better satisfy technical requirements.

Published Japanese patent application 77 143 281 describes the immobilization of enzymes or microbes by a method in which a film is produced on a glass plate from an aqueous polymer dispersion and an enzyme. The product is used in the form of a foil, which optionally may be comminuted.

These prior art solutions are afflicted with serious drawbacks. As a rule, the surface concentration of the immobilized biologically active substances is too low. Also, the reactive surfaces cannot be enlarged at will by comminution of the polymeric supports since small particles tend to be unstable and frequently do not lend themselves to practical use. While it is known (see above) to bind macromolecular compounds to supports by adsorption, the use of such combinations is limited since the compounds can be readily eluted.

Published unexamined German patent application DE-OS 21 12 740 describes a continuous-flow reactor which has a macroporous reaction core having a polymeric surface comprising adsorption-promoting nitrile, acid amide or ureide groups.

After the enzymes have been physically adsorbed on the solid support phase, crosslinking is effected by means of a dialdehyde, for example.

From published unexamined German patent application DE-OS 22 60 184, a method is known for the preparation of macromolecular compounds immobilized on a carrier. In the method, a macromolecular compound A is first reacted with a compound B having at least one functional group capable of coupling with the macromolecular compound A and at least one further functional group capable of polymerizing. Then a molecular-sieve material of a degree of crosslinking which excludes the macromolecular compound A is added in the unswollen state and the polymerizable group of the coupling product AB is polymerized in the molecular-sieve material, optionally together with further monomers.

SUMMARY OF THE INVENTION

It has now been found that high-surface-area systems with reactive units adaptable to the binding of substrates containing nucleophilic groups represent particularly advantageous solutions to the aforementioned problems of the art if the reactive units for the binding of the substrates containing nucleophilic groups are components of a polymer latex, the particles of which are aggregated to form a high-surface-area system and/or are bonded to a high-surface-area support material.

It has further been found that polymer latices in accordance with the claims are particularly well suited for the covalent immobilization of biologically relevant substances and functional units, as earlier defined.

DETAILED DESCRIPTION OF THE INVENTION

Polymer Latex

In the synthesis of the polymer latices in accordance with the present invention, their intended use in the preparation of reactive high-surface-area systems is a decisive influence. The polymer in the latex may therefore be of varying composition, depending on whether it is to be used to produce a thin reactive film on a high-surface-area system, or whether the total surface area of the system formed is to be substantially increased in relation to the surface of the support material by a loosely agglomerated particle structure. When it is desired to produce a thin reactive film on the support material, the latex may be applied to the support at a temperature higher than the minimum film-forming temperature of the polymer in the latex (MFT, as defined in DIN 53787). On the other hand, if the surface area of the support material is to be increased further using the latex, small polymer particles ranging in size from 0.03 to 3 microns, for example, which are intrinsically rigid and do not form films under the conditions of use, will be advantageous. If desired, the non-film-forming latex particles may be bound to one another and to the support by the addition of minor amounts, preferably up to 30 weight percent, of latex particles of a film-forming polymer.

Substrates

The high-surface area systems in accordance with the present invention are generally suited for the immobilization of substrates comprising nucleophilic groups. They are particularly well suited for the immobilization of functionally and/or morphologically defined biologically relevant units or substances, particularly those which are biologically active.

The biologically relevant substances and functional units, which as a rule are capable of interacting with biological systems, are preferably of biological origin and may optionally have been modified from the native form.

Macromolecules, and in particular proteins, here are of primary importance.

Reactive Units/Nucleophilic Groups

The substances or structures which are capable of interacting with biological systems generally comprise groups capable of coupling which are capable of reacting and forming a covalent bond with the reactive units of the polymer latices. The groups usually are nucleophilic groups. Preferably reactive units (functional groups) are used which will react in aqueous solution with stronger nucleophiles than water and which, in the physiologically appropriate pH range, that is to say, in the range from 5.0 to 9.0, and more particularly from 6.5 to 8.0, are not attacked by water or, if so, then only to a minor extent. In selecting the functional groups, it should be borne in mind that the material to be immobilized, and in particular material of biological origin, generally comprises a free amino group as the nucleophilic group, possibly in addition to phenolic, hydroxyl, or thiol groups. Quite generally, the polymer latices in accordance with the invention can be prepared from vinyl compounds susceptible of free-radical polymerization, and preferably comprise monomers which are derivatives of acrylic and/or methacrylic acid, styrene, and/or vinyl esters, and in particular vinyl acetate.

The structure of the polymer latex in accordance with the invention in its reactive form can thus be represented in highly schematized form as follows:

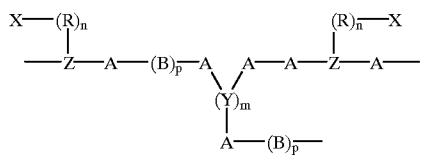

wherein Z represents the polymerized form of a polymerizable group Z', originally present in a polymerizable monomer of the type Z'-(R)$_n$—X, A and B are further monomer components, and Y is a crosslinking unit, all as described more in detail hereinafter. X represents the functional groups for covalent bonding, preferably functional groups which satisfy the conditions described earlier. R represents a spacer between the functional and the polymerizable units; size and type of the spacer are relatively uncritical. Typical examples of such spacers are alkylene groups from $C_1$ to $C_{20}$, and preferably from $C_2$ to $C_{12}$, wherein carbon atoms may optionally be substituted by ether bridges, as well as other units which originally, that is to say, prior to incorporation into the molecule, contain difunctional groups. These units can be linked into the polymer by amide, ester, ether, thioether, urea, urethane, sulfonamide and similar groups both at the "polymer end" and at the "functional end" thereof. Generally the spacer will bring about a separation of the functional groups X from the polymer main chain ranging from 0.5 to 4 nanometers. In a number of examples, the group R may be completely absent, in other words, n may have a value of 0 or 1.

As a rule, X signifies a group susceptible to attack by the nucleophiles in question, that is to say, an activated group, and preferably a sulfonic acid halide or thioisocyanate group, an activated ester group, or a thiocarbonyldioxy, carbonylimidoyldioxy, haloethoxy, haloacetoxy, oxirane, aziridine, formyl, keto, acryloyl, or anhydride group.

Suitable sulfonic acid halides are the chlorides and bromides. Suitable haloacetoxy components are the fluoro, chloro and bromo compounds. Suitable ester components of activated esters are those of hydroxylamine compounds such as N-hydroxysuccinimide or N-hydroxyphthalimide; those of phenols activated by electron-attracting groups, such as nitrophenols or halogen derivatives of phenol, like trichlorophenol; or those of heterocyclic lactams such as pyridone.

Oxirane, keto, formyl, sulfochloride and thioisocyanate groups and activated carboxylic acid esters as well as carboxylic acid anhydrides are particularly preferred.

In the aforementioned monomers of the type Z'-(R)$_n$—X, Z' represents a unit susceptible of free-radical polymerization, and n is 0 or 1.

Such units susceptible of free-radical polymerization include vinyl and vinylidene groups, for example, wherein Z' has the meaning

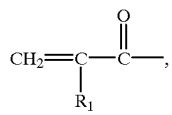

wherein $R_1$ is hydrogen or methyl, or is
—$CH_2$—$COOR_2$, —$CH_2$—$CONHR_2$ or —$CH_2$—$CON(R_2)_2$, $R_2$ signifying alkyl having from 1 to 4 carbon atoms.

Moreover, Z' may be derived from maleic acid:

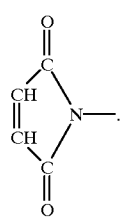

Units which are reactive and at the same time polymerizable further include maleic acid anhydride and itaconic acid anhydride as well as acrolein, methacrolein, methylvinyl ketone, and activated vinyl esters. Particularly preferred are derivatives of acrylic or methacrylic acid and of maleic imide as well as maleic and itaconic anhydride.

The examples which follow will serve to elucidate the Z'-R—X formula scheme:

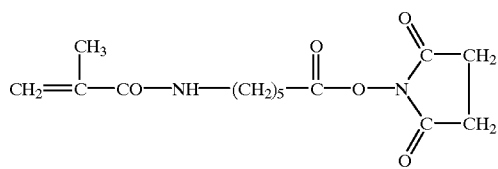

(polymerizable activated ester with a spacer)

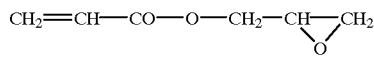

(Glycidyl acrylate)

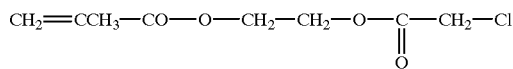

[2-(chloroacetoxy)-ethyl methacrylate]

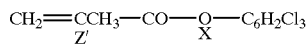

(2,4,5-trichlorophenyl methacrylate) R=0

$CH_2 = C(CH_3) - COO - CH_2 - CH_2 - Br$ (2-bromoethyl methacrylate)

(allyl glycidyl ether)

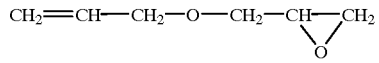

(condensation product of methacrylic acid and 1,4-butanedioldiglycidyl ether)

$CH_2 = CH - COO - CH_2 - CH_2 - O - CSNH - (CH_2)_6 - N = C = S$ (condensation product of acrylic acid-2-hydroxyethyl ester with 1,6-hexanediisothiocyanate)

$CH_2 = CH - O - CO - CH_2 - Cl$ (chloroacetic acid vinyl ester)

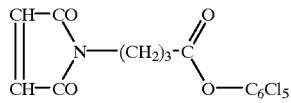

(4-maleimido-butyric acid-pentachlorophenyl ester)

$CH_2 = C(CH_3) - COO - C_6H_4 - SO_2 - CH_3$

[(4-methylsulfonylphenyl)methacrylate]

$CH_2 = CH - COO - CH_2 - C \equiv C - H$ (propargyl acrylate)

The other units which enter into the composition of the polymer latices (A and B in the diagrammatic representation) are, by definition, units which will impart required properties to the latex, in other words, hydrophilicity, if indicated, and appropriate hardness. A guide for the desired hardness in the anhydrous state might be $T_{\lambda max} = -60°$ C. to 200° C., and more particularly $-20°$ C. to 140° C. (in conformity with DIN 53445). On the other hand, the monomers entering into the composition of the polymer latex should preferably contain no strongly nucleophilic groups, such as $-NH_2$ or $-SH$.

Moreover, the components of the polymer latex may be crosslinked. Such crosslinking is symbolized by Y.

The hardness and other relevant properties of the polymers are known from the corresponding properties of the individual monomers, as is the contribution of these properties by monomers to the properties of copolymers. [See U.S. Pat. No. 2,795,564; H. Rauch-Puntigam & T. Volker in "Acryl- und Methacrylverbindungen" ("Acrylic and Methacrylic Compounds"), Springer-Verlag, Berlin, 1967, pp. 303–304; and T. G. Fox, Bull. Am. Phys. Soc. 1, 123 (1956).]

In keeping with the diagrammatic representation, the components which are primarily responsible for the nonhydrophobic, i.e. hydrophilic, character of the polymer latex will be designated B, while further components whose selection must be based mainly on the hardness desired in the resulting overall polymer will be designated A. In other words, in keeping with the differentiation made, the monomers of type A are nonhydrophilic, i.e. hydrophobic.

The subscript p for the monomeric component B in the schematic formula given above indicates that the monomer A, which is to be used mainly to impart appropriate hardness to the overall polymer, must be coordinated with component B with respect to its amount. The value of p can therefore range from zero to a value that corresponds to a proportion of B of the overall polymer of 95 weight percent, and preferably of from 0 to 60 weight percent. The conditions specified for the polymer latex to be used in accordance with the invention are satisfied by copolymers of the methacrylate and/or acrylate type. Their qualitative and quantitative proportion must be such that they can be aggregated or bound to a carrier to form a system of high surface area.

Suitable nonhydrophobic or hydrophilic components B are, for example, optionally substituted methacrylamides and acrylamides of the general formula

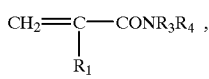

wherein $R_1$ is hydrogen or methyl and $R_3$ and $R_4$ are, independently of each other, hydrogen or alkyl having from 1 to 4 carbon atoms. In other words, these compounds are unsubstituted amides as well as amides formed with primary and secondary amines, and include compounds wherein $R_3$ and $R_4$, together with the nitrogen atom, form an optionally alkyl-substituted ring which may contain one or more additional heteroatoms, in particular atoms of nitrogen or oxygen. Included are, in particular, acrylamide and methacrylamide, N-methyl-(or -isopropyl- or -butyl-)-acrylamide and methacrylamide, N,N-dimethylacrylamide and the corresponding methacrylamide, as well as acrylic acid or methacrylic acid morpholide (a special case in which the nitrogen is part of a ring through $R_3$ and $R_4$), and N-vinyl-2-pyrrolidone.

In addition, acrylate- or methacrylate-type monomers containing hydroxyl groups, and in particular hydroxyl-group-containing esters or amides of acrylic and methacrylic acid, as well as alkoxyalkyl esters and/or amides of acrylic and methacrylic acid, are suitable as hydrophilic monomers of type B, for example, compounds represented by the general formula

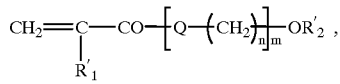

wherein $R'_1$ is hydrogen or methyl, $R'_2$ is hydrogen or an alkyl group having from 1 to 4 carbon atoms, Q is oxygen or a —$NR''_2$—group wherein $R''_2$ represents hydrogen or an alkyl group having from 1 to 4 carbon atoms, n is an integer from 1 to 3, and preferably 2, and m is an integer from 1 to 25, a condition being that when Q stands for oxygen, n must not be equal to 1. Specifically included are hydroxyethyl acrylate and methacrylate, 2-hydroxyethyl-acrylamide and -methacrylamide, 2-hydroxypropyl-acrylamide and -methacrylamide, and monoesters of acrylic and methacrylic acid with glycerol and other polyhydric alcohols.

The type B monomer further includes sulfoethyl-acrylates and -methacrylates as well as sulfoethyl-acrylamides and -methacrylamides. Polymerizable acids such as acrylic acid and methacrylic acid, itaconic acid and maleic acid, and polymerizable tertiary amines such as 2-N,N-dimethylaminoethyl-acrylamide or -methacrylamide and 2-N,N-dimethylaminoethyl-acrylic acid and -methacrylic acid esters, and 3-N,N-dimethylaminopropyl-acrylamide or methacrylamide and the corresponding acrylic acid or methacrylic acid esters are also suitable for incorporation as hydrophilic groups in the latex particles. To avoid imparting a net electrical charge to the latex particles, these acidic or basic groups should always be present simultaneously in a particle (e.g. methacrylic acid and 2-N,N-dimethylaminoethyl methacrylate), so that the particles are substantially electrically neutral.

Suitable type A monomers are monomers which are not soluble or are only sparingly soluble in water. The qualitative and quantitative proportion thereof must be such that the hardness criterion specified supra for the resulting polymer is satisfied. The monomers include:

(a) Esters of acrylic and/or methacrylic acid with $C_1$ to $C_{20}$ alcohols, and in particular the methyl, ethyl, propyl, and butyl esters of methacrylic acid, as well as the methyl, ethyl, propyl, butyl, and 2-ethylhexyl esters of acrylic acid; and (b) copolymerizable monomers of the vinyl ester type, and in particular vinyl acetate, vinyl propionate, vinyl butyrate and vinyl isobutyrate.

Since component A is coordinated with the other components, the proportion which A represents of the overall polymer can vary widely and may, for example, range from 0 to 99 weight percent, and preferably from 20 to 99 weight percent, based on the overall polymer.

In addition to the monomeric components described above, the polymer latices in accordance with the invention may contain crosslinking monomers. (Y in the diagrammatic representation.) The index m may be 0 or 1; in other words, the crosslinking agent may be absent.

The term "crosslinking monomers" here means what it usually does, namely monomers which, for example, contain two or more reactive double bonds in the molecule, such as dihydric or polyhydric alcohols esterified with acrylic acid or, preferably, methacrylic acid, as well as allyl compounds such as allyl methacrylate, triallyl cyanurate, etc.

For example, ethylene glycol dimethacrylate, 1,4-butanediol dimethacrylate, triglycol dimethacrylate, and trimethylolpropane trimethacrylate are included.

The proportion of crosslinking agent, if any, will depend on the hydrophilicity of the overall polymer. With increasing hydrophilicity of the latex particles, an increasing proportion of crosslinking agent will be advantageous. It will generally range from 0 to 50 weight percent, and preferably from 0.2 to 15 weight percent, based on the overall polymer.

The proportion which the functional monomers represent of the overall polymer may vary widely, depending on the particular monomers actually used. For example, while the covalent binding of the substrate having nucleophilic groups thereon requires at least 0.1% of the Z'-R—X monomer, the maximum content of this monomer depends markedly on the monomer used. When the reactive monomer itself possesses some hydrophilicity or hydrolyzes in some measure to a hydrophilic compound under the conditions of preparation of the polymer dispersions, the proportion of this Z'-R—X monomer may be as high as 99.9 weight percent. (In the case of glycidyl methacrylate, for example, the remaining 0.1% will be a crosslinking agent such as 1,4-butanediol dimethacrylate.)

0.1 weight percent, based on the overall polymer, may thus be regarded as a guide for the lower limit, and 99.9 weight percent as a guide for the upper limit, the preferred range being 1 to 50 weight percent.

Preparation of polymer latices

The latex dispersions may be prepared by the known rules of emulsion polymerization, for example, as described in German published unexamined patent applications DE-OS 18 04 159, DE-OS 19 10 488, and DE-OS 19 10 532, the desired size of the latex particles being determined by the emulsifier concentration at the start of polymerization. In general, the emulsifier concentration at the start of the emulsion polymerization will be between 0.005 and 0.5 weight percent, based on the total polymer batch. The latex particles should range in size from 0.03 to 6 microns, and preferably from 0.03 to 1 micron. Suitable emulsifiers are the known anionic and nonionic emulsifiers, for example, sulfates, and sulfonates, phosphates, and phosphonates of fatty alcohols; alkali-metal salts of long-chain fatty acids; long-chain sarcosides; hydroxyethylated fatty alcohols; substituted phenols which may be partially sulfonated; and other emulsifiers used in emulsion polymerization. [Houben-Weyl, Methoden der Organischen Chemie ("Methods of Organic Chemistry"), Vol. XIV/I, pp. 133–560, G. Thieme-Verlag, 1961.]

So far as cationic surfactants are concerned, only those derived from tertiary or quaternary ammonium salts are recommended. Emulsifiers which can be incorporated into the polymer during polymerization may also be used.

The initiators, too, may be those conventionally used in emulsion polymerization. (See J. Brandrup & E. H. Immergut, Polymer Handbook, 2nd Ed., J. Wiley & Sons; H. Rauch-Puntigam & Th. Völker: "Acryl- und Methacrylverbindungen", Springer-Verlag, 1967.) Among these are peroxides, hydroperoxides, peracids, and azo compounds, for example, potassium persulfate, hydrogen peroxide, etc.

As a rule, the concentration of the initiators will be in the usual range, for example, 0.01 to 1.0 weight percent, based on the monomers.

The solids content of the dispersions may range from 10 to 60 weight percent, depending on the size and hydrophilicity of the particles.

The synthesis of the latex particles must be carried out under conditions which are sufficiently mild so that the functional groups contributed by the Z'-R—X monomers remain largely intact; only then is the subsequent covalent binding of molecules with =NH, —SH and —COOH groups possible.

It should be noted that preservation of the functional groups from the Z'-R—X monomers (which groups are susceptible to nucleophilic attack) in or on the surface the latex particles will be the more difficult the more hydrophilic the composition of the latex particles is.

The following example will serve to demonstrate this.

With fully similar preparation [synthesis temperature=80° C.; pH=7.0; polymerization time (emulsion feed)=4 hours; addition of the glycidyl methacrylate reactive monomer only during the 4th hour of the 4-hour feed; further heating for 1 hour at 80° C.], the dispersions compared below are found to have the following oxirane-group content:

| | Gross composition of polymer | Oxirane group content of latex* |
|---|---|---|
| 42.5% | Methyl methacrylate | |
| 42.5% | Isobutyl methacrylate | |
| 5% | Ethylene glycol dimethacrylate | 71% |
| 10% | Glycidyl methacrylate | |
| 40% | Methyl methacrylate | |
| 40% | Isobutyl methacrylate | |
| 5% | Ethylene glycol dimethacrylate | 15% |
| 10% | Glycidyl methacrylate | |
| 5% | Methacrylamide | |

*)Based on glycidyl methacrylate used

Requirements for preparation of the latex particles under mild conditions are:

(1) The dispersion must be prepared in a pH range in which the rate of reaction of water with the reactive groups is minimal (as a rule, this will be a pH of about 7);

(2) preparation must take place at as low a temperature as possible;

(3) the polymerization time must be as short as possible; and (4) strong nucleophiles must not be present in the latex particles.

Concerning (1): Synthesis of the latex particles in the neutral pH range is accomplished most readily by buffering the system (with a phosphate buffer, for example). In some cases, buffering by the addition of a salt may be dispensed with altogether, for example, when other components of the formulation act as buffering agents, as when alkali-metal salts of long-chain phosphoric acid esters are used as emulsifiers or when the sodium salt of 4,4'-azobiscyanovaleric acid is used.

Concerning (2) and (3): Items (2) and (3) call for minimum thermal stress of the latex particles carrying the reactive groups. However, this is subject to the following qualification: Since the content of reactive groups at the latex surface is of primary importance, it is perfectly possible to use said reactive groups only in the production of the outer envelope of the latex particles. For example, a core/shell structure may be used wherein the latex core is completely free of reactive monomers. In that case, the requirement that the latex be prepared under mild conditions applies only to the shell, of course.

Polymerization is carried out either at low temperatures (for example, under 50° C.) with the use of a redox system, care being taken that the reactive groups are not destroyed by components of the redox system (as, for example, the oxirane groups by bisulfite), or else with thermally-decomposing initiators or with the aid of a redox system at temperatures of up to 90° C. The polymerization time should not exceed 8 hours.

Concerning (4): Since the latex contains reactive groups which are to make possible the covalent binding of molecules containing =NH, —SH or —OH groups, such groups must be present in the latex only to a minor extent. This applies especially to =NH and —SH groups. The presence of —OH groups in the latex is less critical.

Preparation of high-surface-area systems

The polymer latices in accordance with the invention are preferably applied to suitable carriers or supports.

Suitable supports are, in the first place, inert and generally water-insoluble supports, and in particular solid supports preferably having as large a surface area as possible. From a practical point of view, porous bodies are particularly well suited for use as supports. These include also foamed materials and sponges, for example, as well as fibrous structures, nonwoven fabrics, etc. Both organic and inorganic support materials are suitable for use.

Examples of the latter are supports comprising silica or a silicate and in particular finely divided silica, for example, in the form of gels or as "Aerosil", and also supports comprising alumina and/or other metal oxides and comprising clays such as fuller's earth, etc., and ceramics, as well as finely divided inorganic pigments such as titanium dioxide and barite; also chalk, talc, gypsum, pumice, glass, activated charcoal, stainless steel, etc. A honeycombed material comprising cordierite ($Mg_2Al_4Si_5O_{18}$), for example, also appears to be suitable.

Supports of organic origin include both modified natural products and synthetic materials of a polymeric nature. Suitable natural products are, in particular, fibrous protein structures, for example, wool and those comprising a carbohydrate (cellulose, starch, and especially crosslinked dextranes, etc.). Materials comprising synthetic polymers, for example, polyamides, polyesters, PMMA, polyurethane, polyacrylonitrile and polyimide foams, are also suitable.

These substances are of special interest when they are used in sheet form, for example, as nonwovens, wadding or (unsized) paper, or as corresponding three-dimensional macroporous bodies.

The reactive latex particles described above may be applied to high-surface-area materials such as paper, wadding, nonwovens, etc., as well as to inorganic support materials, by conventional impregnation, spraying or other techniques.

Two different bonding mechanisms are involved in such application:

(1) The latex forms a film at the temperature of application

In this case, a latex mass is used which is smaller than the mass of the support material (solid/solid) so that the total surface area of the support material is not reduced.

(2) The latex does not form a film at the temperature of application and/or use

In this case, the ratio of latex (solid substance) to support substance may range from 1:100 to 100:1, depending on the nature of the surface of the support material.

Optionally, a solid support may be dispensed with altogether in this case. This requires agglomeration of the latex by spray drying, freeze drying, or precipitation (with sodium sulfate, for example) or by other methods such as coagulation by the action of heat, by freezing, or by the effect of solvents, so that an internal surface of maximum area is preserved.

When the individual latex particles are not bound together by film formation, they can be bonded together or to the support by covalent bonds. In the case of latex particles containing oxirane groups, such bonding can be accomplished by reaction of the oxirane ring with the —OH groups of adjacent latex particles or with —OH groups of the support material, for example. If desired, such covalent bonding of the latex particles may be enhanced by the use of multifunctional nucleophiles, for example, polyamines. However, the latex particles can also be bound to the support or to one another by means of secondary valence bonds or minor amounts of a soft, film-forming substance, for example, latex particles of a polymer having a lower glass transition temperature. These soft latex particles may also contain functional groups.

In a particularly preferred embodiment, the functionally and/or morphologically defined biologically active units themselves are used in precipitation. Thus, a protein to be bound, for example an enzyme, may itself be used as a multifunctional crosslinking agent. This approach can be used especially with latex particles of very small size.

The high-surface-area systems are used as catalysts (for example after the immobilization of enzymes thereon) according to the kind of specific support material (in a fixed bed, for example). The dispersions, spray-dried or precipitated with a salt or in the presence of enzymes, are preferably used in a batch or fluidized bed. While these materials have high porosity and very high catalytic activity, their mechanical strength is low. In case the substrate, containing nucleophilic groups, which is to be bonded is not already present during the agglomeration of the latex particles, the reaction of the substrate with the high-surface-area reactive system takes place under the usual conditions. [For example, binding of the enzyme trypsin to a support containing oxirane groups in a unimolar phosphate buffer (pH 7.5) over a period of 72 hours at 23° C.] Functionally and/or morphologically defined biologically active units or substances in general may be used as substrates. These include, for example, proteins generally, and in particular enzymes, blood constituents and blood factors (blood-group substances and Rh factors), for example, albumins, immunoglobulins, blood-clotting factors, cell-membrane proteins, peptide hormones and the like. They further include high-molecular-weight biogenic substances, which optionally may be impregnated with dyes for use in diagnostics, for example. In addition to being used as catalysts, these also lend themselves to use in affinity chromatography and for diagnostic purposes generally.

When so used, for example in the form of a test paper, it may be advantageous also physically or covalently to incorporate a dye, which may be pH- or redox-sensitive for example. Now, for example, when a substrate is also present, the other reactant, for example an enzyme, can be identified by a color change.

For diagnostic purposes, the reactive latex may be applied to paper strips or to test rods of any desired support material.

When dry, the test strips or test rods which have reacted with the reagent (for example, an enzyme substrate) and, optionally, also with a dye) can then be stored for any length of time provided that certain temperature conditions are maintained.

The actual test can be made at the proper time simply by dipping the test strip or test rod into a medium (for example, urine, blood serum, etc.) containing the reactant (for example, an enzyme). In addition to these specific diagnostic applications, the high-surface-area system can be used generally as an indicator having biological affinity. When it is used as a catalyst, for example a biocatalyst, the reactive latex particles may be used in two basically different versions.

When used in a fixed bed, the latex particles are generally applied to one of the support materials described above. The reaction with the catalyst can take place before or after such application. Because of their high specificity and selectivity, enzymes here are of primary interest. However, more simply structured and nonspecifically acting groups (for example, quaternary ammonium compounds or imidazole and other heterocyclic compounds for catalysis of a hydrolysis) may be used.

The reactive high-surface-area systems in accordance with the invention are suited for the immobilization of all classes of enzymes, for example, oxidoreductases, transferases, hydrolases, lyases, isomerases and ligases. Thus, the high-surface-area systems of the invention are suited for the immobilization of enzymes suited for therapeutic use and adaptable to oral administration, for example proteases and/or lipases and/or amylases.

Unsupported latex aggregates in particular, which can be employed in powder form or as a slurry or in another coarsely dispersed form, are suitable for use in a fluidized bed, in addition to comminuted support/catalyst combinations that can also be used in a fixed bed. Reaction with the enzyme substrate can take place either with the original latex itself or after its agglomeration. The catalysts described earlier in connection with fixed-bed catalysis can be used here, too.

When a chemical reaction requires that several enzymes intervene in the reaction process, the problem frequently arises that these enzymes are unable to coexist. In the case of covalent bonding to the claimed support materials, it is often possible to minimize or even eliminate such incompatibilities. Thus, using the method of the present invention, it is quite possible to immobilize two or more different enzymes. However, it may also be advantageous directly to use enzyme combinations present in a cellular aggregate, in other words, to immobilize whole microorganisms. This can be done particularly advantageously with the claimed reactive latex particles. The accessibility of such a system to the substrate can be readily controlled through the amount and particle size of the particles. In this way, higher-molecular-weight substrates can also be reacted.

Suited for such embedment or immobilization are, in particular:

(1) Viruses, prokaryotes and eukaryotes and subunits thereof [see (2)] as well as cellular hybrids such as are used in the production of monoclonal antibodies, for example; and (2) organelles, and in particular of mitochondria and microsomes, membrane parts, nuclei and subunits thereof.

The latex particle/support combinations in accordance with the present invention are used in affinity chromatography in much the same way as described in connection with their use as catalysts, except that the reactive molecules to be bound to the reactive latex are tailored to the particular end use. One possible use of the high-surface-area systems of the invention is as sorbents having biological affinity.

It is perfectly possible that overlapping may occur. For example, a bound enzyme which can be used as catalyst may be used in the chromatographic purification of an enzyme inhibitor.

A particularly interesting use of the supports involves the elimination of traces of toxic substances, as in the lavage of blood, in water conditioning, etc. The reactive high-surface-area system can be similarly used, as in the removal of nucleophilic impurities from aqueous media, for example, the removal of toxic amines, mercaptans and other pollutants from aqueous media. Moreover, the high-surface-area systems in accordance with the invention can be reacted with multifunctional substances containing at least one nucleophilic group (for bonding to the latex particle) and at least one further functional group which is capable of specific interaction with substances or functional units contained in the aqueous medium. Groups having the capacity for such specific interaction may be complexing agents, for example, such as the reaction product of amino-diacetic acid with an oxirane-containing latex and the like.

Further possible uses of the reactive high-surface-area system of the invention involve its use as stationary phase in preparative organic chemistry. Thus, a latex containing disulfide bridges obtained in this way may be used as a mild oxidizing agent, for example, in which case elimination of the mercaptan formed can be dispensed with.

The use of the reactive high-surface-area system in accordance with the present invention as stationary phase in preparative peptide synthesis is of particular interest. The peptide may be synthesized on the high-surface-area system or the latter may take up activated reactants, for example amino acids having pronounced coupling capacity or coupling agents such as difficultly soluble carbodiimides. In the latter case, the peptide to be synthesized remains dissolved in the aqueous phase.

In principle, both a latex-particle/active-substance combination bound to a solid support and a loosely aggregated latex-particle/active-substance combination (column) are usable in chromatography.

The following examples have been selected to illustrate the immobilization principle in accordance with the invention.

EXAMPLE 1

Preparation of a dispersion containing oxirane groups

A solution of 10 g phosphate buffer solution, pH 7.0 ("Titrisol", Merck), 0.4 g sodium salt of 4,4'-azobis-(4-cyanovaleric acid), 0.3 g sodium lauryl sulfate, and 555 g distilled water is introduced into a polymerization vessel equipped with a reflux condenser, a stirrer, and a thermostat, and, is heated to 80° C.

To this solution there is added dropwise over a period of 4 hours, also at 80° C., an emulsion prepared from 360 g methyl methacrylate, 210 g butyl acrylate, 30 g glycidyl methacrylate, 2 g sodium salt of 4,4'-azobis-(4-cyanovaleric acid), 3 g sodium lauryl sulfate, and 840 g distilled water.

Agitation is continued for another 2 hours at 80° C. and the contents of the vessel are then cooled to room temperature and filtered. A coagulate-free dispersion is obtained. Solids content, about 30%; pH value, 7.3; viscosity, 2 mPa.sec.

EXAMPLE 2

Preparation of a dispersion containing oxirane groups

A solution of 50 g phosphate buffer solution, pH 7.0 ("Titrisol", Merck), 0.3 g sodium lauryl sulfate, 0.3 g sodium salt of 4,4'-azobis-(4-cyanovaleric acid), and 515 g distilled water is introduced into a polymerization vessel equipped with a reflux condenser, a stirrer, and a thermostat, and is heated to 80° C.

To this solution there is added dropwise over a period of 4 hours, also at 80° C., an emulsion prepared from 300 g methyl methacrylate, 210 g butyl acrylate, 90 g glycidyl methacrylate, 2 g sodium salt of 4,4'-azobis-(4-cyanovaleric acid), 3 g sodium lauryl sulfate, and 840 g distilled water.

Stirring is continued for another 90 minutes at 80° C. the contents of the vessel are then cooled to room temperature and filtered. A readily filterable, coagulate-free dispersion is obtained. Solids content, about 30%; pH value, 7.1; viscosity, 1 mPa.sec.

EXAMPLE 3

Preparation of a dispersion containing oxirane groups

A solution of 6.5 g sodium lauryl sulfate, 0.6 g sodium salt of 4,4'-azobis-(4-cyanovaleric acid), 10.0 g phosphate buffer solution, pH 7.0 (Titrisol, Merck), and 600.0 g distilled water is introduced into a polymerization vessel equipped with a reflux condenser, a stirrer, and a thermostat and is heated to 80° C.

To this solution there is added dropwise over a period of 3 hours, at 80° C., an emulsion prepared from 18 g methacrylamide, 11 g ethylene glycol dimethacrylate, 150 g methyl methacrylate, 180 g glycidyl methacrylate, 1.5 g sodium lauryl sulfate, 2.0 g sodium salt of 4,4'-azobis-(4-cyanovaleric acid), and 900 g distilled water.

Stirring is continued for another 30 minutes at 80° C. and the contents of the vessel are then cooled to room temperature and filtered. A readily filterable, coagulate-free dispersion is obtained. Solids content, 19.4%; pH value, 7.7; viscosity, 2 mPa.sec.

EXAMPLE 4

Preparation of a dispersion containing oxirane groups

The same procedure is followed as in Example 3 except that an emulsion with a different monomer composition is metered in.

Monomer composition 18 g methacrylamide 36 g ethylene glycol dimethacrylate 125 g methyl methacrylate 180 g glycidyl methacrylate Auxiliary substances, polymerization time and polymerization temperature are the same as in Example 3.

A readily filterable, coagulate-free dispersion is obtained.
Solids content, 19.7%; pH value, 7.6; viscosity, 1 mPa.sec.

EXAMPLE 5

Immobilization of the enzyme ribonuclease by reaction with latex according to Example 4

100 mg pancreatic ribonuclease (E.C. 2.7.7.16) (Merck, Article No. 24570) are dissolved in 1 ml 0.05M phosphate buffer, pH 7.5. To this solution there is added, with stirring, 1 ml of the dispersion of Example 4. This mixture is allowed to stand for 3 days at 23° C.

For working up, the mixture is suspended three times in 50 ml portions of 1M NaCl solution and then centrifuged. This washing operation is repeated twice with 50 ml 0.05M phosphate buffer.

Yield: 1.1 g moist substance.

Determination of enzyme activity was carried out by alkalimetric titration at 37° C. and pH 7.5 with RNA as substrate. (For this and subsequent samples, 3 or 4 subsequent determinations ["cycles"] are carried out to discriminate between bound and unbound trypsin.)

| Cycle | Moist weight (g) | Activity* U/g moist weight |
|---|---|---|
| 1 | 1.10 | 101 |
| 2 | 1.75 | 54.8 |
| 3 | 1.74 | 51.0 |
| 4 | 1.68 | 55.0 |
| 5 | 1.71 | 51.9 |

*)1 U corresponds to 1 micromol/min, measured on the basis of the initial rate.

EXAMPLE 6

Immobilization of the enzyme trypsin by reaction with a latex according to Example 4

The same procedure is followed as in Example 5, except that 100 mg bovine trypsin (E.C. 3.4.4.4) (Merck, Article No. 24579) is used as an enzyme.

Determination of enzyme activity is carried out by alkalimetric titration at 37° C. and pH 7.5 ($N^\alpha$-benzoyl-L-arginine ethyl ester hydrochloride=BAEE as substrate) and pH 8.0 (casein).

| Cycle | Activity (U/g)* (Substrate: BAEE) | Activity (U/g)* (Substrate: Casein) |
|---|---|---|
| 1 | 174 | 42.5 |
| 2 | 163 | 26.7 |
| 3 | 161 | 23.3 |
| 4 | 161 | 23.3 |

*)Activities based on moist weight; 1 U corresponds to 1 micromol/min, measured on the basis of the initial rate.

EXAMPLES 7 TO 11

Immobilization of the enzyme trypsin by reaction with a latex according to Example 4

The same procedure is followed as in Example 6, except that the enzyme/latex ratio was varied.

| | Activity: | | | |
|---|---|---|---|---|
| Ex. | Initial weight trypsin (mg) | Initial weight latex solid (mg) | Ratio of trypsin to latex solid | Activity (U/g)* (Substrate: Casein) |
| 7 | 20 | 200 | 1:10 | 3.7 |
| 8 | 40 | 200 | 1:5 | 13.8 |
| 9 | 80 | 200 | 1:2.5 | 22.2 |
| 6 | 100 | 200 | 1:2 | 23.3 |
| 10 | 160 | 200 | 1:1.25 | 26.4 |
| 11 | 200 | 200 | 1:1 | 22.3 |

*)Activity measured in each case upon the third cycle.

EXAMPLE 12

Immobilization of the enzyme penicillin amidase by reaction with a latex according to Example 4

The same procedure is followed as in Example 5, except that 100 mg penicillin amidase (*Escherichia coli* E.C. 3.5.1.11)) is used as the enzyme.

Determination of enzyme activity is carried out by measurement at 37° C. and pH 7.8. (Substrate: Potassium penicillin G.)

Activity measurement
First cycle: 42.7 U/g initial moist weight
Second cycle: 42.0 U/g initial moist weight
Third cycle: 41.6 U/g initial moist weight

EXAMPLE 13

Immobilization of the enzyme ribonuclease by reaction with a latex according to Example 3

The same procedure is followed as in Example 5, except that the latex of Example 3 is used to crosslink the enzyme.

Activity measurement
First cycle: 68.5 U/g initial moist weight
Second cycle: 61.8 U/g initial moist weight
Third cycle: 61.8 U/g initial moist weight
Fourth cycle: 61.0 U/g initial moist weight

EXAMPLE 14

Immobilization of the enzyme ribonuclease on a paper activated by impregnation with a dispersion containing oxirane groups 100 ml of the dispersion of Example 1 are diluted with 500 ml distilled water. With this approximately 5% dispersion, a sheet of paper (Whatman Medium Flow) measuring about 100 $cm^2$ is impregnated. After being pressed, the paper is kept at room temperature for 1 hour and then dried for 30 minutes at 80° C. The paper so treated contains 20 g of polymer solids per square meter. This reactive paper can be stored for at least 12 months at temperatures under −15° C.

Immobilization of the Enzyme Ribonuclease 100 mg pancreatic ribonuclease (Merck, Article No. 24570) are dissolved in 2 ml of 0.05M phosphate buffer (pH 7.5). The resulting solution is used to impregnate the paper treated with the latex particles containing oxirane groups, the paper then being allowed to stand for 72 hours at 23° C. After being pressed, the paper is washed three times with a 1N NaCl solution and twice with an 0.05M phosphate buffer solution (pH 7.5).

Activity measurement (third cycle): 2 U/g moist paper. Conditions: 37° C., pH 7.5.

EXAMPLE 15

The same procedure was followed as in Example 14, except that the trypsin enzyme of Example 6 is used.

Activity measurement (third cycle): 2.5 U/g moist paper. Substrate: BAEE; pH 7.5; 37° C.

EXAMPLE 16

The same procedure is followed as in Example 14, except that a more concentrated dispersion (100 ml of the dispersion of Example 1, diluted with 200 ml distilled water) is used to impregnate the paper.

Drying conditions: 12 hours at 25° C. in a circulating-air drying cabinet.

Polymer solids per square meter of paper: 33 g.

The enzyme trypsin is then immobilized as described in Example 14 with respect to the enzyme ribonuclease.

Activity measurement (third cycle): 4.1 U/g moist paper. Substrate: BAEE; pH 7.5, 37° C.

EXAMPLE 17

The same procedure is followed as in Example 16, except that the latex of Example 2 (diluted as in Example 16; 100 ml dispersion in 200 ml distilled water) is used for impregnation.

Polymer solids per square meter of paper: 27 g. Activity measurement (third cycle): 7 U/g moist paper. Substrate: BAEE; pH 7.5, 37° C.

EXAMPLE 18

100 ml of the dispersion of Example 1 is diluted with 200 ml distilled water and then used to spray absorbent cotton (thickness, 2 mm), which is then dried for 12 hours at room temperature.

Polymer solids per square meter of cotton: 39 g. Activity measurement (third cycle; ribonuclease as in Example 5)=2.1 U/g moist cotton.

The conditions of measurement are as described in Example 14.

EXAMPLE 19

The procedure followed is the same as in Example 14, the paper being impregnated with the dispersion of Example 1 containing oxirane groups, followed by drying and reaction with the enzyme ribonuclease of Example 5. However, the paper treated for 72 hours with the enzyme solution is also treated for 24 hours, without further purification, with an 0.005% solution of 4'-aminoazobenzene-2-carboxylic acid in a 0.05M phosphate buffer solution, and is then washed three times with a 1N NaCl solution and twice with a 0.05M phosphate buffer solution (pH 7.5).

For use as an indicator (substrate detection), the paper is then washed another two times with a 1N NaCl solution.

In the presence of a substrate, the paper changes color from yellow to orange.

Activity of test strip at pH 7.5 (37° C.): 1.5 U/g moist weight.

EXAMPLE 20

Immobilization of *Escherichia coli* by reaction with the latex of Example 4

10 ml of the dispersion of Example 4 are added to 10 ml of a 20% cell suspension of *Escherichia coli* in a physiological saline solution. The mixture is allowed to stand at room temperature for 24 hours.

A network is obtained that can readily be purified by centrifugation.

| Activities: Substrate: Potassium penicillin (2%); 37° C. | |
|---|---|
| Cycle | Activity (U/g moist catalyst) |
| 1 | 118 |
| 2 | 66 |
| 3 | 55 |
| 4 | 53 |

The activities of the immobilized *Escherichia coli* are quite comparable to those of nonimmobilized *Escherichia coli* (shown below):

| Cycle | Activity |
|---|---|
| 1 | 128.5 |
| 2 | 132.5 |
| 3 | 132.5 |

EXAMPLE 21

Preparation of a dispersion utilizing a seed latex

In a polymerization flask equipped with a reflux condenser, stirrer, and thermometer, 1600 g of water are kept at 80° C.

After addition of 3 g of isobutylmethacrylate, 3 g of methylmethacrylate, 0.3 g of ethylenglycoldimethacrylate, and 0.8 g of sodium lauryl sulfate, 4 g of ammonium persulfate dissolved in 36 g of water are added.

At 80° C. a mixture of 200 g of isobutylmethacrylate, 200 g of methyl methacrylate, and 20 g of ethylenglycol dimethacrylate is then added dropwise within 2 hours.

After the addition has been completed, the mixture is stirred for another hour at 80° C.

A coagulate-free dispersion of low viscosity is obtained (solids content ca. 20%), which in the following will be referred to as "dispersion i)".

In a polymerization flask equipped as described above, 330 g of water together with 10 ml of a phosphate buffer solution of pH7 ("Titrisol") to which 160 g of dispersion i) have been added are heated to 80° C. 0.4 g of the sodium salt of 4,4'-azobis-(4-cyanovaleric acid) in 4 ml of water are added to this mixture.

Afterwards an emulsion consisting of 1000 g of water, 1 g of sodium lauryl sulfate, 2 g of sodium salt of 4,4'-azobis-(4-cyanovaleric acid), 160 g of ethyl acrylate, and 145 g of isobutyl methacrylate is added within 3 hours at 80° C. Thereafter a solution of 10 g of methacrylamide and 0.6 g of the sodium salt of 4,4'-azobis-(4-cyanovaleric acid) in 300 ml of water and a monomer mixture consisting of 50 g of ethyl acrylate and 45 g of glycidyl methacrylate are added simultaneously. After stirring for 60 minutes at 80° C. one obtains a coagulate-free dispersion with a solid content of 20%.

EXAMPLE 22

Impregnation of chromatography paper

A sheet of chromatography paper (Whatman No. 1, medium flow) was cut in rectangular pieces of 10×20 mm.

Using forceps, the pieces of paper were dipped into the undiluted dispersions as prepared in Example 21. Excess liquid is disposed of at the edge of a beaker and the pieces of paper are dried by pinning them on a cork board and leaving them there at room temperature overnight.

Such pieces of paper (test strips) were stored in plastic bottles at −15° C. in a deep freezer.

For the purpose of control, strips were prepared essentially as described above making use of a dispersion modelled on Example 21, but not containing any epoxy groups.

EXAMPLE 23

Impregnation of acrylic glass 50 ml of an undiluted dispersion prepared according to Example 21 are equally distributed on one side of a sample of PMMA glass measuring 10×20 mm (1 mm high) and are allowed to dry at room temperature overnight.

The acrylic glass samples were stored in a deep freezer at −15° C.

Controls were prepared in analogy to the paper strips of Example 22.

EXAMPLE 24

Immobilization of Anti-Human-Globulin (from goat) on paper strips and acrylic glass samples Antihuman-IgG-Rhodamine from goat (obtained through Miles-Yeda Ltd, Rehovoth/Israel) containing 1.5–2.0 mg of antibody per milliliter was diluted in a ratio 1:10 down to 1:100 with 0.5 molar potassium phosphate buffer (pH 7.5).

Paper strips as prepared in Example 22 or acrylic glass pieces as prepared in Example 23 are transferred, each separately into glass vials of 2.4 mm diameter. To each vial one ml of the IgG-solution as previously prepared is added and the vials are firmly sealed. After keeping them at 23° C. for 40 hours, the paper strips or the pieces of acrylic glass respectively are washed ten times with 1 ml portion of potassium phosphate buffer (0.1 molar) at pH7.5.

Only the strips which had been previously treated with a dispersion containing oxirane groups (e.g. according to Example 21) display a red color.

The same color effect is observed with the pieces of acrylic glass. The red fluorescence displayed by the IgG-Rhodamine fixed to the surfaces can be measured quantitatively using a fluorescence photometer as used in thin layer chromatography.

In the case of the controls consisting of a) uncoated paper and acrylic glass, and b) paper and acrylic glass coated with a dispersion free of oxirane groups, no appreciable formation of red color nor measurable red fluorescence can be observed.

EXAMPLE 25

Removal of excess oxirane groups after IgG-immobilization

Paper strips or pieces of acrylic glass are prepared according to Example 24 with the only difference that anti-human-IgG did not contain any rhodamine. They were kept under one milliliter of one of the following solutions at 23° C. for 72 hours:

a) 10% glycine in 0.5 molar potassium phosphate buffer (pH 8.0), b) 5% human albumin in 0.5 molar potassium phosphate buffer (pH 8.0), or c) 1% ethanolamine in water.

The samples are washed afterwards ten times with 1 ml of water each.

Thereafter the paper strips as well as the acrylic glass pieces were treated with Rhodamine-anti-human-IgG as described in Example 24.

Result: No appreciable formation of red color nor measurable red fluorescence could be observed.

EXAMPLE 26

Examples 21, 22, 23, 24 and 25 may be carried out with essentially the same results with a modified type of dispersion. Thus in Example 21, in the last step of polymerization the monomers are replaced as follows:

25 g of hydroxy ethyl methacrylate instead of 10 g of methacrylamide, 70 g of ethylacrylate instead of 50 g of ethyl acrylate, 5 g of methacrolein instead of 45 g of glycidyl methacrylate.

With such a dispersion immobilization of IgG requires shorter reaction times (approximately 1 hour).

EXAMPLE 27

Example 26 may be conveniently modified by exchanging 5 g of methacrolein for 5 g of the methacrylic ester of N-hydroxysuccinimide.

The resulting dispersions may be employed as the ones in Examples 21 through 25.

What is claimed is:

1. A system of high surface area, adaptable to the immobilization thereon of a substance having a nucleophilic group, comprising discrete particles of a polymer latex bonded to a porous support of high surface area, said particles having thereon oxirane groups reactive with the nucleophilic group of the substance to be immobilized.

2. A system as in claim 1 wherein said latex particles are bonded to said support by applying said latex to said support and drying said latex.

3. A system as in claim 1 wherein said latex particles bonded to said support are particles of a non-film-forming polymer.

4. A system as in claim 1 wherein said polymer comprises at least one member selected from the group consisting of compounds of acrylic acid, compounds of methacrylic acid, styrene, and vinyl acetate.

5. A system as in claim 1 wherein said oxirane groups will react with a substance containing a nucleophilic bond in aqueous solution in the pH range from 5 to 10 with formation of a covalent bond.

6. A system as in claim 1 wherein said support comprises an organic material.

7. A system as in claim 6 wherein said organic material is selected from the group consisting of vinyl polymers, carbohydrates, proteins, polyamino acids, polyamides, and polyesters.

8. A system as in claim 1 wherein said support is a nonwoven fabric.

9. A system as in claim 1 wherein said support is wadding.

10. A system as in claim 1 wherein said support is a foam.

11. A system as in claim 1 wherein said support comprises an inorganic material.

12. A system as in claim 11 wherein said inorganic support material is a nonwoven fabric.

13. A system as in claim 11 wherein said inorganic support material is a porous body.

14. A system as in claim 11 wherein said inorganic support Material is selected from the group consisting of silica, silicates, metal oxides, clays, sand, ceramics, coal, or stainless steel.

15. A system as in claim 1 which further comprises a pH-sensitive dye or a redox-sensitive dye.

16. A system as in claim 1 having a catalyst immobilized thereon.

17. A system as in claim 1 having a biocatalyst with enzymatic activity immobilized thereon.

18. A system as in claim 1 having an enzyme having therapeutic utility immobilized thereon.

19. A system as in claim 18 wherein said immobilized enzyme is a member selected from the group consisting of proteases, lipases, and amylases.

20. A method comprising using a system as in claim 1 as a sorbent having biological affinity to sorb ad separate a biological substance.

21. A method for removing pollutants containing nucleophilic groups from an aqueous medium by contacting said aqueous medium with a system as in claim 1.

22. A method of organic synthesis wherein a system as in claim 1 is used as a stationary phase.

23. A method as in claim 22 wherein said synthesis is a peptide synthesis.

24. A method of treating a patient requiring therapeutic treatment which comprises orally administering to said patient a system as in claim 18.

25. A method of immobilizing a substance having a nucleophilic group on a system of high surface area, which method comprises reacting a nucleophilic group of said substance with an oxirane group present on discrete particles of a polymer latex bonded to a support.

26. A method as in claim 25 wherein said substance which is immobilized is a member of the group consisting of functionally defined and morphologically defined biologically active materials.

27. A method as in claim 25 wherein said substance which is immobilized is a protein.

28. A method as in claim 25 wherein said substance which is immobilized is an enzyme.

29. A method as in claim 25 wherein said substance which is immobilized is a blood protein or blood factor.

30. A method as in claim 25 wherein said substance which is immobilized is selected from the group consisting of albumin, immunoglobulins, blood-clotting factors, cell-membrane proteins, and peptide hormones.

31. A method as in claim 25 wherein said substance which is immobilized is a biogenic substrate of high molecular weight.

32. A method as in claim 31 wherein said biogenic substrate of high molecular weight is covalently bonded with a dye.

* * * * *

UNITED STATES PATENT AND TRADEMARK OFFICE
CERTIFICATE OF CORRECTION

PATENT NO. : 5,976,527

DATED : November 2, 1999

INVENTOR(S): Werner SIOL et al.

It is certified that an error appears in the above-identified patent and that said Letters Patent is hereby corrected as shown below:

On the title page, item [30], the Foreign Application Priority Data is incorrectly listed. It should be:

--[30]   Foreign Application Priority Data

Aug. 5, 1981   [DE]   Germany...........31 30 924--

On the title page, item [73] is incorrect. It should read as follows:

--[73] Roehm GmbH Chemishe Fabrik, Darmstadt, Germany--

Signed and Sealed this

Third Day of April, 2001

*Attest:*

NICHOLAS P. GODICI

*Attesting Officer*   Acting Director of the United States Patent and Trademark Office